(12) United States Patent
Matsumoto et al.

(10) Patent No.: US 10,342,511 B2
(45) Date of Patent: Jul. 9, 2019

(54) ULTRASOUND TRANSDUCER ELEMENT AND ULTRASOUND ENDOSCOPE

(71) Applicant: OLYMPUS CORPORATION, Tokyo (JP)

(72) Inventors: Kazuya Matsumoto, Nagano (JP); Katsuhiro Wakabayashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 746 days.

(21) Appl. No.: 14/711,176

(22) Filed: May 13, 2015

(65) Prior Publication Data

US 2015/0245811 A1 Sep. 3, 2015

Related U.S. Application Data

(63) Continuation of application No. PCT/JP2013/078935, filed on Oct. 25, 2013.

(30) Foreign Application Priority Data

Nov. 15, 2012 (JP) .................................. 2012-251444

(51) Int. Cl.
*A61B 8/00* (2006.01)
*A61B 8/12* (2006.01)
*B06B 1/02* (2006.01)
*H01L 49/02* (2006.01)

(52) U.S. Cl.
CPC .............. *A61B 8/4483* (2013.01); *A61B 8/12* (2013.01); *B06B 1/0292* (2013.01); *H01L 28/60* (2013.01)

(58) Field of Classification Search
None
See application file for complete search history.

(56) References Cited

U.S. PATENT DOCUMENTS

| 6,262,946 | B1 | 7/2001 | Khuri-Yakub et al. |
| 6,854,338 | B2 | 2/2005 | Khuri-Yakub et al. |
| 2005/0018536 | A1* | 1/2005 | Caliano ................ B06B 1/0292 367/7 |

(Continued)

FOREIGN PATENT DOCUMENTS

| EP | 1992290 A1 | 11/2008 |
| JP | 2007-229327 A | 9/2007 |

(Continued)

OTHER PUBLICATIONS

Pappalardo et al., "Capacitive Ultrasonic Transducers with a New Vibrating Structrure," Oct. 5, 2003, IEEE Ultrasonics Symposium, pp. 1955-1959.*

(Continued)

*Primary Examiner* — Patricia J Park
(74) *Attorney, Agent, or Firm* — Scully, Scott, Murphy & Presser, P.C.

(57) ABSTRACT

An ultrasound transducer element including a cell group constituted by a plurality of ultrasound transducer cells, wherein each of the plurality of ultrasound transducer cells includes a lower electrode arranged on a substrate, a membrane including an upper electrode arranged facing the lower electrode with a cavity positioned therebetween, and a plurality of pillars forming the cavity by supporting the membrane, and each cavity mutually communicates with one another.

7 Claims, 13 Drawing Sheets

(56) References Cited

U.S. PATENT DOCUMENTS

| | | | |
|---|---|---|---|
| 2007/0013269 A1 | 1/2007 | Huang | |
| 2007/0167812 A1* | 7/2007 | Lemmerhirt | B06B 1/0292 |
| | | | 600/459 |
| 2008/0089180 A1* | 4/2008 | Matsumoto | A61B 8/12 |
| | | | 367/181 |
| 2009/0076393 A1 | 3/2009 | Adachi et al. | |

FOREIGN PATENT DOCUMENTS

| | | |
|---|---|---|
| JP | 2008-546239 A | 12/2008 |
| JP | 2011-035916 A | 2/2011 |
| WO | WO 2006/123298 A2 | 11/2006 |
| WO | WO 2007/099696 A1 | 9/2007 |
| WO | WO 2010/053032 A1 | 5/2010 |

OTHER PUBLICATIONS

International Search Report dated Nov. 26, 2013 issued in PCT/JP2013/078935.
Balasunder, R.I. et al., "Ultrasound Therapy Transducers With Space-Filling Non-Periodic Arrays", IEEE Transactions on Ultrasonics, Ferroelectrics and Frequency Control, May 1, 2011, vol. 58, No. 5, pp. 944-954.
Extended Supplementary European Search Report dated Jul. 6, 2016 in related European Application No. 13 85 4660.1.

* cited by examiner

ULTRASOUND TRANSDUCER ELEMENT AND ULTRASOUND ENDOSCOPE

CROSS REFERENCE TO RELATED APPLICATION

This application is a continuation application of PCT/JP2013/078935 filed on Oct. 25, 2013 and claims benefit of Japanese Application No. 2012-251444 filed in Japan on Nov. 15, 2012, the entire contents of which are incorporated herein by this reference.

BACKGROUND OF INVENTION

1. Field of the Invention

The present invention relates to an ultrasound transducer element (hereinafter also referred to an "element") provided with a cell group constituted by a plurality of capacitive ultrasound transducer cells (hereinafter also referred to as "cells"), and an ultrasound endoscope provided with an insertion portion with the ultrasound transducer element arranged at a distal end portion.

2. Description of the Related Art

An ultrasound diagnostic method of radiating an ultrasound to an inside of a body and performing imaging of a state inside the body from an echo signal to make a diagnosis has been spreading. One of medical apparatuses used for the ultrasound diagnostic method is an ultrasound endoscope. In the ultrasound endoscope, an element is arranged at a distal-end rigid portion of an insertion portion to be introduced into an inside of a body. The element has a function of converting an electrical signal to an ultrasound and transmitting the ultrasound into the body, and a function of receiving an ultrasound reflected inside the body and converting the ultrasound to an electrical signal.

For a lot of today's elements, ceramic piezoelectric materials including lead, which is environmentally very hazardous, for example, PZT (lead titanium zirconium oxide), are mainly used. On the other hand, development of an element manufactured with the use of MEMS (micro electro mechanical systems) has been advanced, the element having a plurality cells constituted by capacitive micro-machined ultrasonic transducers (hereinafter referred to as "c-MUTs") the material of which does not include lead.

For example, an element 120 shown in FIGS. 1 to 3 is disclosed in specification of U.S. Pat. No. 6,854,338. As shown in FIG. 1, which is a top view, the element 120 has cells 110 constituted by twenty-five c-MUTs, which are a base unit of ultrasound transmission/reception.

FIG. 2 is a cross-sectional view of one of the cells 110 of the element 120. FIG. 3 is a partially exploded view of four of the cells 110 of the element 120 shown in FIG. 1, and a regular square indicated by broken lines shows an area exclusive to one cell 110, in other words, a plane view shape of the cell 110. Note that the plane view shape will be hereinafter referred to simply as a shape below. The shape of the cell 110 can be regarded as a regular square.

As shown in FIGS. 2 and 3, the cell 110 has a conductive substrate 111, which is also a lower electrode 112, and an upper electrode 116 arranged facing the substrate 111, with a cavity 114H therebetween. An area of the upper electrode 116 immediately above the cavity 114H constitutes a membrane 118 which ultrasonically vibrates. The cavity 114H is formed by a through hole formed in an insulating layer 114. The cavity 114H is a sealed space isolated from an outside.

When a drive signal is applied between the lower electrodes 112 and the upper electrodes 116, the membranes 118 vibrate, and the cells 110 generate an ultrasound. When an ultrasound comes in from the outside, the ultrasound is converted to an electrical signal by utilizing a fact that the membranes 118 are deformed, and capacitance between the electrodes changes. The larger an aperture ratio indicated by "(an area of the membranes 118)/(an area of the cells 110)", the higher a transmission/reception sensitivity of the element 120 is.

In the element 120 having the regularly square cells 110, areas other than areas of the membranes 118 immediately above the circular cavities 114H are non-sensitive areas which do not contribute to transmission/reception of an ultrasound. For example, capacitance between the electrodes in the non-sensitive areas is so-called parasitic capacitance which does not change at a time of receiving an ultrasound.

SUMMARY OF THE INVENTION

An ultrasound transducer element of an embodiment of the present invention is an ultrasound transducer element including a cell group constituted by a plurality of ultrasound transducer cells, wherein each of the plurality of ultrasound transducer cells includes a lower electrode arranged on a substrate, a membrane including an upper electrode arranged facing the lower electrode with a cavity positioned therebetween, and a plurality of pillars forming the cavity by supporting the membrane, and each cavity mutually communicates with one another.

An ultrasound endoscope of another embodiment is an ultrasound endoscope including: an insertion portion with an ultrasound transducer element arranged at a distal end portion thereof, the ultrasound transducer element including a cell group constituted by a plurality of ultrasound transducer cells; an operation portion arranged on a proximal end side of the insertion portion; and a universal cord extending from the operation portion; wherein each of the plurality of ultrasound transducer cells includes a lower electrode arranged on a substrate, a membrane including an upper electrode arranged facing the lower electrode with a cavity positioned therebetween, and a plurality of pillars forming the cavity by supporting the membrane, and each cavity mutually communicates with one another.

DETAILED DESCRIPTION OF THE PREFERRED EMBODIMENT(S)

First Embodiment

Figure 4:
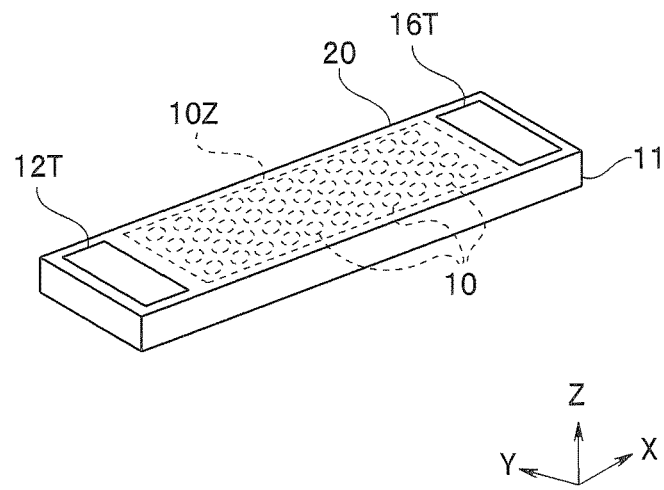
FIG. 4 is a perspective view of an element of a first embodiment.

As shown in FIG. 4, in an ultrasound transducer element 20 of the present embodiment, a cell group 10Z constituted by a plurality of ultrasound transducer cells 10 is arranged on a substrate 11. When a drive signal is applied between a lower electrode terminal 12T and an upper electrode terminal 16T, the cell group 10Z transmits an ultrasound, and the incident ultrasound is converted to an electrical signal on the basis of change in capacitance between the lower electrode terminal 12T and the upper electrode terminal 16T, and received.

Figure 5:
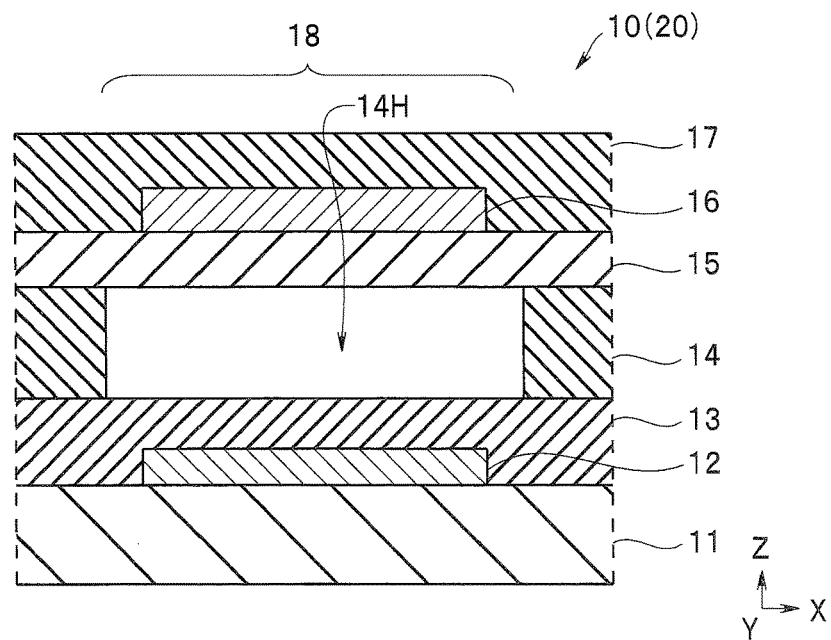
FIG. 5 is a cross-sectional view of an ultrasound transducer cell of the element of the first embodiment.

As shown in FIG. 5, the cell 10 has a lower electrode 12 connected to the lower electrode terminal 12T, a lower insulating layer 13 covering the lower electrode 12, pillars 14 forming a cavity 14H, and a membrane 18 which is supported by the pillars 14 and includes an upper electrode 16 connected to the upper electrode terminal 16T. An area of the membrane 18 immediately above the cavity 14H includes an upper insulating layer 15, the upper electrode 16, and a protective layer 17.

The pillars 14 form the cavity 14H by supporting the membrane 18. As described later, the cavity 14H is a space in a vacuum or a space in which desired gas is sealed at a desired gas pressure.

Note that, though an insulating film is formed on a surface of the substrate 11 made of single crystal silicon or the like, the film is not shown. The lower electrode 12 is a single-layer film or a multi-layer film made of conductive metal, for example, Al, Mo, W, Ti or an alloy of the metals.

Note that graphene, silicene or the like may be used for the upper electrode 16 in order to thin thickness of the membrane 18. Graphene has a two-dimensional net structure or a structure in which a plurality of two-dimensional net structure layers are laminated, the structure being constituted by carbon atoms. Silicene has a two-dimensional net structure constituted by silicon atoms. Graphene and the like have conductivity, high rigidity and high thermal conductivity equal to those of a metal though its thickness is very small.

The lower insulating layer 13, the upper insulating layer 15 and the pillars 14 are made of silicon nitride, silicon oxide, tantalum oxide, hafnium oxide or the like. The lower insulating layer 13, the upper insulating layer 15 and the pillars 14 may be made of different materials, respectively. Note that at least either the lower insulating layer 13 or the upper insulating layer 15 is not an indispensable component.

The lower insulating layer 13 protects the lower electrode 12 during a process and guarantees electrical insulation between the lower electrode 12 and the upper electrode 16. A surface of the lower insulating layer 13 formed as a film such that it covers the lower electrode 12 is flattened by a CMP method or the like as necessary after being formed as the film.

The cavity 14H is formed by sacrificing layer etching. That is, the pillars 14 and a sacrificing layer are arranged on the lower insulating layer 13 and covered with the upper insulating layer 15 or the like.

Then, by forming a through hole (VIA hole) in the upper insulating layer 15 or the like covering the sacrificing layer, etchant is injected into the sacrificing layer. Then, by selectively etching the sacrificing layer, the cavity 14H, which is a cavity portion, is formed. Material of the sacrificing layer is selected from among materials having a high etching selectivity relative to surrounding material. For example, when the lower insulating layer 13 and the like are made of silicon nitride, phosphorus glass or the like is used for the sacrificing layer. The VIA hole is plugged after etching of the sacrificing layer. A hole plugging member may be used as a part of the pillars 14.

The upper electrode 16 is made of material similar to that of the lower electrode 12. The protective layer 17 covering the upper electrode 16 is constituted by an insulator made of silicon nitride, silicon oxide, polyimide, polyparaxylylene or the like.

Note that materials of components of the element 20, a manufacture method of the element 20 and the like are almost the same as those of the conventional element. That is, the element 20 is different from the conventional element in that it is not the insulating layer 114 but the multiple pillars 14 that support the membrane. Therefore, the manufacture method and the like of the element 20 are not limited to the description above, and a well-known element manufacture method and the like can be used.

Figure 1:
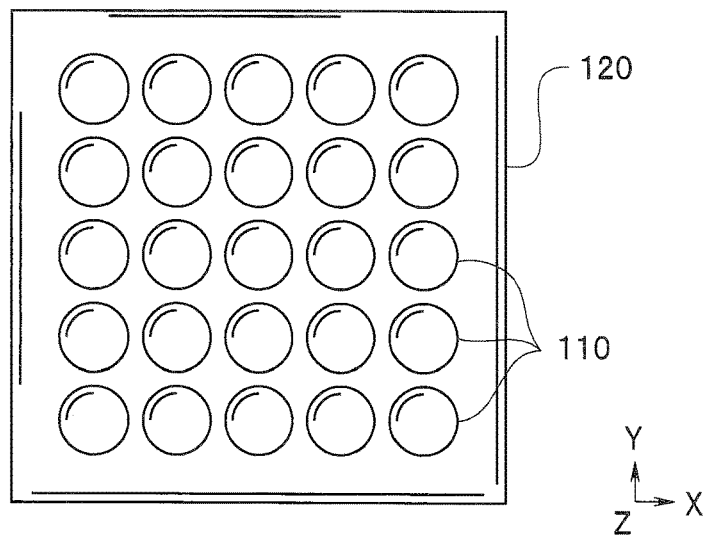
FIG. 1 is a top view of a conventional element.
Figure 2:
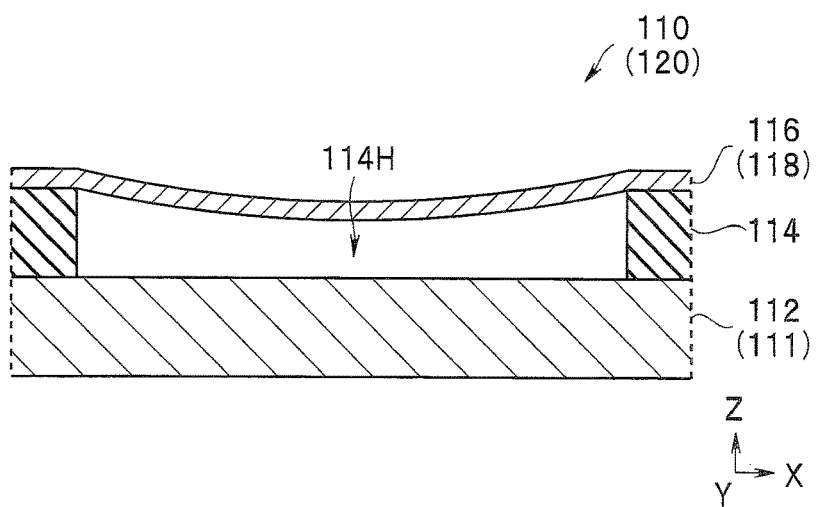
FIG. 2 is a cross-sectional view of an ultrasound transducer cell of the conventional element.
Figure 3:
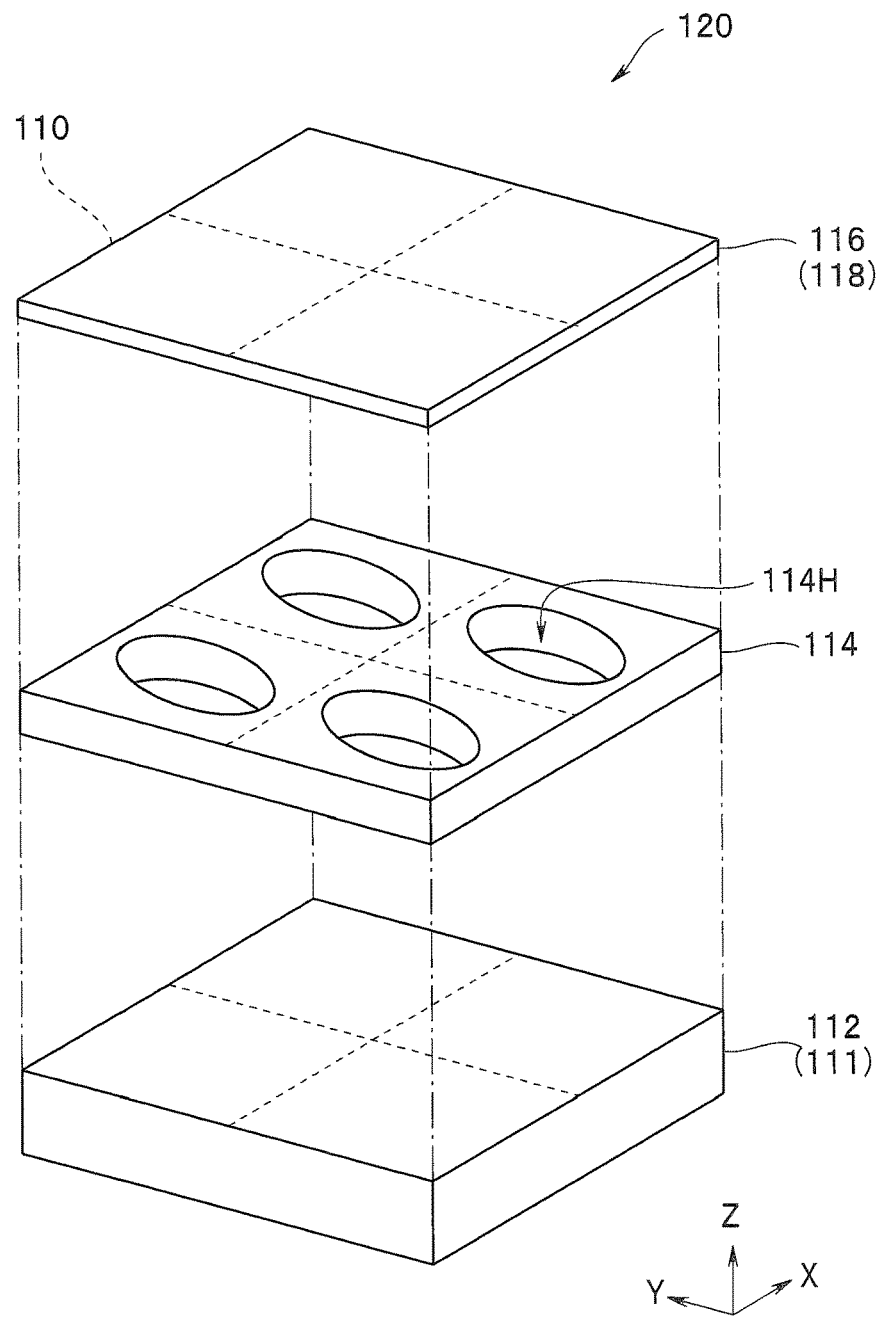
FIG. 3 is an exploded view of the conventional element.
Figure 6:
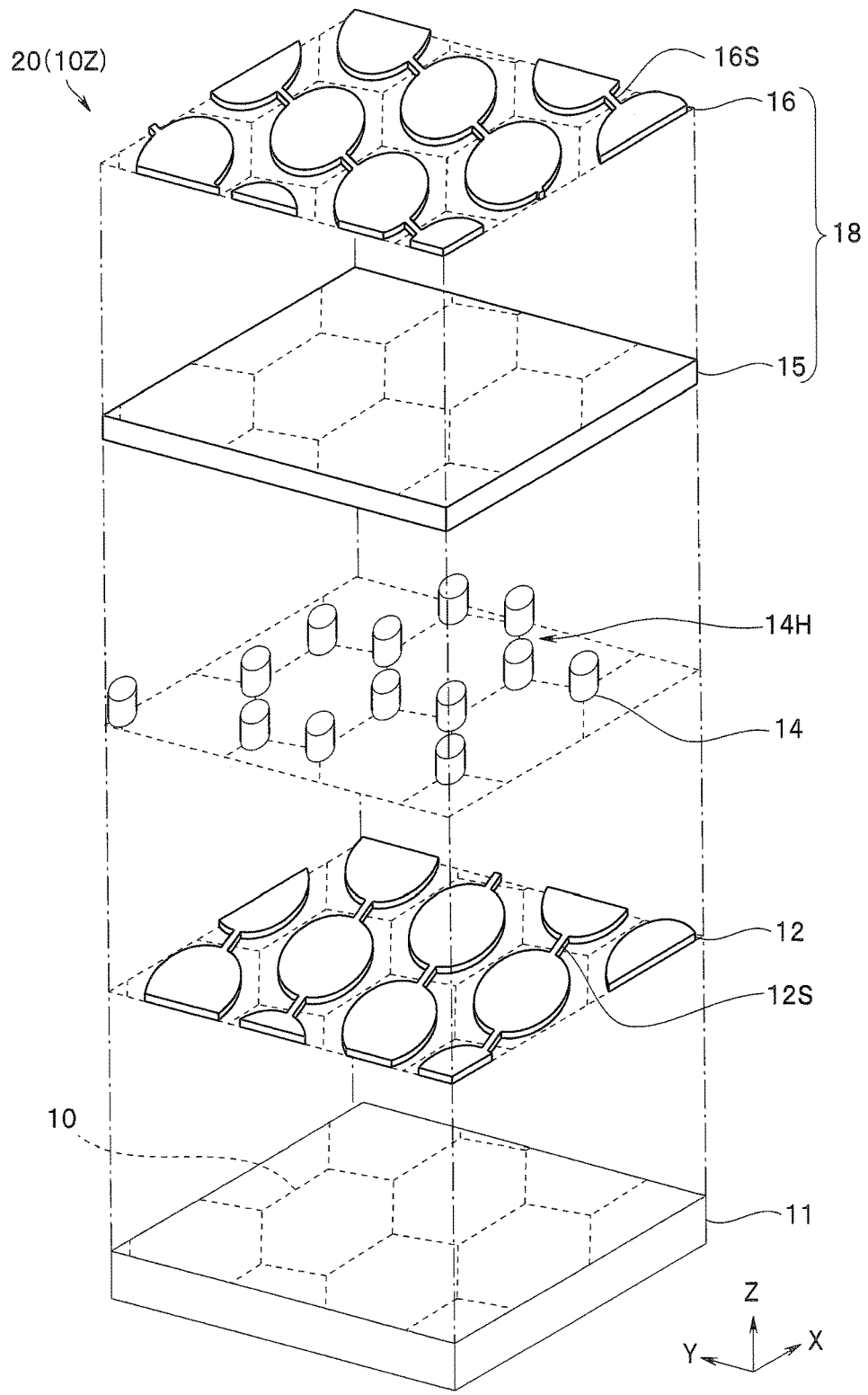
FIG. 6 is an exploded view of the element of the first embodiment.

The cell 10 shown in FIG. 5 appears to resemble the cell 110 shown in FIG. 2. However, as shown in FIG. 3, each cavity 114H is a sealed space in the conventional element 120. In other words, each cavity 114H is isolated. In comparison, the cavity 14H is formed by the plurality of pillars 14 in the element 20 as shown in FIG. 6. Therefore, the plurality of cavities 14H of the cell group 10Z are so-called open cavities which communicate with one another. In other words, the plurality of cavities 14H form one space.

Figure 7:
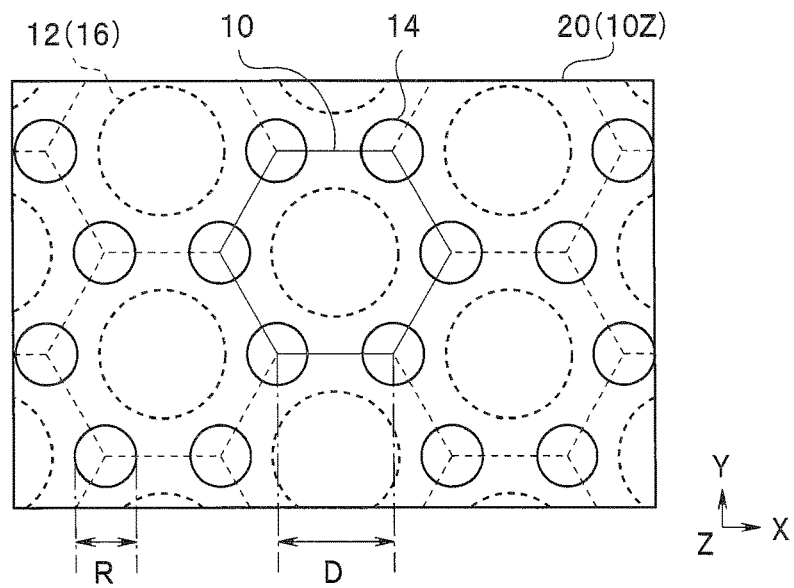
FIG. 7 is a schematic top view for illustrating the cells of the element of the first embodiment.

Note that the lower insulating layer 13 and the protective layer 17 are not shown in the exploded view of FIG. 6. Further, the top view of FIG. 7 shows only arrangement of the pillars 14, the lower electrodes 12 and the upper electrodes 16. Each regular hexagon shown by a broken line in FIGS. 6 and 7 indicates an area exclusive to one cell 10, in other words, a plane view shape of the cell 10. Actually, however, borders are not clearly shown. For example, borderlines of the cavities 14H of the plurality of cells 10 shown by broken lines are virtual lines which do not actually exist.

As shown in FIGS. 6 and 7, the plurality of cells 10 each of which has a regularly hexagonal plane view shape are closely arranged in the element 20. That is, each pillar 14 supports the membranes 18 of three adjoining cells 10, and thereby the cavities 14H are formed. An area where the upper insulating layer 15 is joined to the pillar 14 is a non-sensitive area which does not vibrate and does not contribute to transmission/reception. However, an aperture ratio of area of a vibration area of the membrane 18 relative to area of the cell in the element 20 is much higher than that of the conventional element. That is, the shape and area of the cell 10 are almost equal to the shape and area of the cavity 14H.

Note that, strictly, the shape of the cell 10 and the shape of the cavity 14H excluding the areas of the pillars 14 are different from each other in the element 20 also, but the shape of the cavity 14H may be hereinafter referred to as the shape of the cell 10.

The lower electrodes 12 of the plurality of cells 10 are connected with one another via lower electrode wiring 12S, and the upper electrodes 16 are connected with one another via upper electrode wiring 16S. That is, the plurality of cells 10 of the element 20 constitute the cell group 10Z the cells of which are simultaneously driven.

When electric potential that is not zero is applied between the lower electrodes 12 and the upper electrodes 16 via the lower electrode terminal 12T and the upper electrode terminal 16T, the membranes 18 are drawn to a direction of the lower electrodes 12 by electrostatic attraction generated by potential difference and displaced. Note that it is preferable from a viewpoint of ensuring safety that potential of the upper electrodes 16 be ground potential.

Displacement of the membrane 18 is maximized at a central point of the cell 10, and, on borders with adjoining cells, is the largest at a bisection point of each side of the regular hexagon. Further, the displacement is in a line symmetry, with borderlines with the adjoining cells 10 indicated by broken lines as axes. Further, since the cell 10 is a regular hexagon, the displacement is in a six-fold symmetry in which the displacement becomes equal when rotated by sixty degrees relative to the central point of the cell 10.

When the applied potential is cut off in a state that the membranes 18 are displaced, electrostatic attraction disappears. The membranes 18 vibrate at a resonance frequency determined by constituent material and a structure parameter, and an ultrasound with a number of vibrations equal to the resonance frequency is transmitted.

Note that it is preferable to, in a case of transmitting an ultrasound like a pulse, control a waveform and the like of a drive signal to be applied. For example, it is preferable to, in order to enable displacement of the membranes 18 to follow increase of the applied potential, increase the potential slowly or apply a next pulse after a sufficient time period so that the membranes 18 completely stop vibration. Further, after transmission of the ultrasound, the membranes 18 may be forcedly caused to stop vibration by attraction by application of an auxiliary pulse or by generation of counter vibration by application of an auxiliary pulse with a phase opposite to that of a main pulse.

On the other hand, in a case of successively transmitting ultrasounds for Doppler measurement or the like, a drive signal with a frequency equal to the resonance frequency of the membranes 18, for example, a drive signal constituted by a triangular wave pulse is applied.

A vibration frequency of the membranes 18 at a time of occurrence of an ultrasound, that is, a frequency of the generated ultrasound is slightly lower than a frequency of an ultrasound generated by cells each of which has a circular cavity inscribed in the regularly hexagonal cell 10. In order to realize an ultrasound frequency equal to that of the cells having the inscribed circular cavities, the cell 10 can be reduced in a similar shape.

When an ultrasound enters the cells 10, the membranes 18 vibrate at a frequency of the incident ultrasound by sound pressure of the ultrasound. In response to the vibration, thickness of the cavities 14H, that is, a distance between the electrodes changes, and the capacitance between the electrodes changes in response thereto. Therefore, by detecting the capacitance between the electrodes, an intensity and frequency of the incident ultrasound are detected.

Note that, by continuously keeping the membranes 18 infinitesimally deformed using a DC offset/bias method in which potential difference is continuously applied between electrodes, the element 20 can transmit and receive an ultrasound with a higher frequency.

Note that the drive signal may be supplied from an outside of the element 20, or a drive circuit constituted by an IC or the like may be arranged on a back of the element 20.

Here, it is preferable that a diameter R of a section of the pillar 14, which is a cylinder, be between $\frac{1}{20}$ and $\frac{1}{5}$ of a distance D between pillars 14, inclusive, as shown in FIG. 7. If the diameter R is within the range or larger, it is possible to stably support the membranes 18. If the diameter R is within the range or smaller, the aperture ratio is large, for example, 95% or above, and, therefore, the transmission/reception sensitivity is high.

For example, in a case where the distance D and the diameter R are 100 μm and 10 μm in the regularly hexagonal cell 10, respectively, area of the cell 10 is 26000 μm2, and area of the pillar 14 is 157 μm2. Therefore, the aperture ratio is (26000−157)/26000=99.4%.

In comparison, in the conventional element in which cells are arrayed in a square lattice, each of the cells having an isolated circular cavity, the aperture ratio is "(area of circle)/(area of square circumscribed in the circle)" and, therefore, 78.5% even in a case where the cavities are virtually adjoin one another.

That is, though the aperture ratio is below 80% in the conventional element in which cells are arrayed in a square lattice, each of the cells having an isolated circular cavity, it is possible to easily realize a high aperture ratio exceeding 95% in the element 20.

Improvement of the ultrasound transmission/reception sensitivity of the element 20 is achieved, and, further expansion of application/development becomes possible. That the aperture ratio is large means that efficient driving of the membranes is possible or that a parasitic capacitance ratio decreases, and a signal-to-noise ratio (SN ratio) increases.

That is, the aperture ratio of the element 20 is large, and its transmission/reception sensitive is high.

Furthermore, in the element 20, all areas where the lower electrode 12 and the upper electrode 16 face each other contribute to reception of an ultrasound, and the reception sensitivity is high because of not being influenced by parasitic capacitance by a non-sensitive area.

Figure 8A:
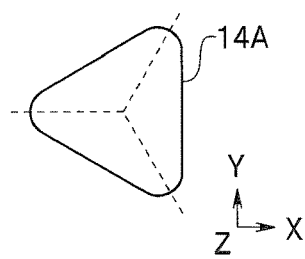
FIG. 8A is a diagram showing a modification of a pillar of the element of the first embodiment.
Figure 8B:
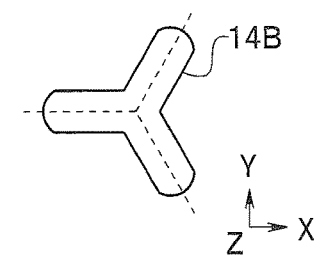
FIG. 8B is a diagram showing a modification of the pillar of the element of the first embodiment.
Figure 8C:
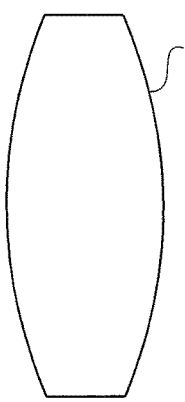
FIG. 8C is a diagram showing a modification of a pillar of the element of the first embodiment.
Figure 8D:
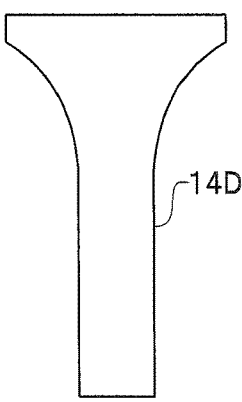
FIG. 8D is a diagram showing a modification of a pillar of the element of the first embodiment.

Note that a shape of the pillar 14 is not limited to a cylinder. For example, a section of a pillar 14A shown in FIG. 8A is not circular but almost regularly triangular. A pillar 14B shown in FIG. 8B is almost star-shaped, with its crosses projecting in three directions. Further, a pillar 14C shown in FIG. 8C is in an entasis shape with its central part expanded, and a pillar 14D shown in FIG. 8D is in a decorated pillar shape, with its upper part expanded.

The pillar 14 may be in a shape such as an elliptic cylinder, a polygonal column, a star-shape column, a cone or a polygonal pyramid. Further, the plurality of pillars 14 of the element 20 may be constituted by a plurality of pillars in different shapes. Note that it is preferable that the pillars 45 be designed so that the aperture ratio of the cells is 90% or higher, preferably 95% or higher even in a case of the pillars 45 in a shape other than a cylinder.

Second Embodiment

Figure 9:
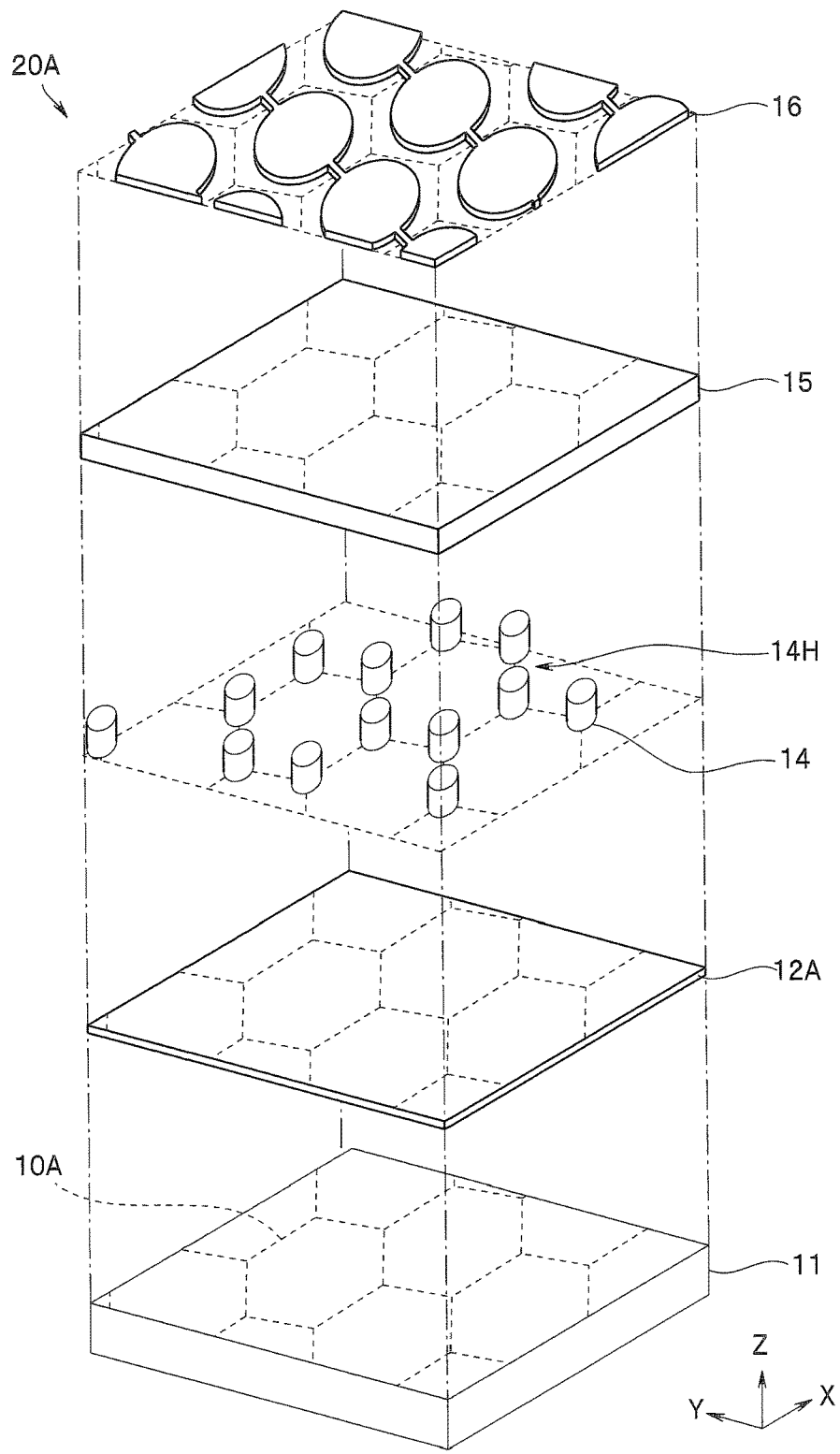
FIG. 9 is an exploded view of an element of a second embodiment.

Since an element 20A of a second embodiment shown in FIG. 9 resembles the element 20, same components are given same reference numerals, and description thereof will be omitted.

In the element 20A, lower electrodes 12A are lower electrodes common to a plurality of cells 10A, which is arranged on a whole surface of an area where a cell group 10ZA is formed. That is, though the lower electrodes 12A of the respective cells 10A are shown by broken lines in FIG. 9, the border lines are virtual lines.

In the element 20A, the lower electrodes 12A are arranged on the whole surface. However, since all areas where the upper and lower electrodes face each other are included in the membranes 18, it does not happen that a non-sensitive area increases in comparison with the element 20 having the patterned lower electrodes 12.

Since it is not necessary to perform patterning of the lower electrodes 12A, the element 20A is easy to manufacture. Further, as already described, since unevenness is formed on the surface of the lower insulating layer 13 formed on the patterned lower electrodes 12 as a film, it is preferable to flatten the surface. In the element 20A, however, since the lower electrodes 12A are arranged on the whole surface of the area where the cell group 10ZA is formed, unevenness is not formed on the surface of the lower insulating layer 13, and it is unnecessary to perform flattening.

The element 20A has effects of the element 20. Further, the element 20A is easy to manufacture.

Note that it goes without saying that, even if at least either the lower electrodes 12 or the upper electrodes 16 are arranged on the whole surface of the area of the substrate 11 where the cell group 10Z is faulted, effects similar of those of the element 20A are provided.

Third Embodiment

Figure 10:
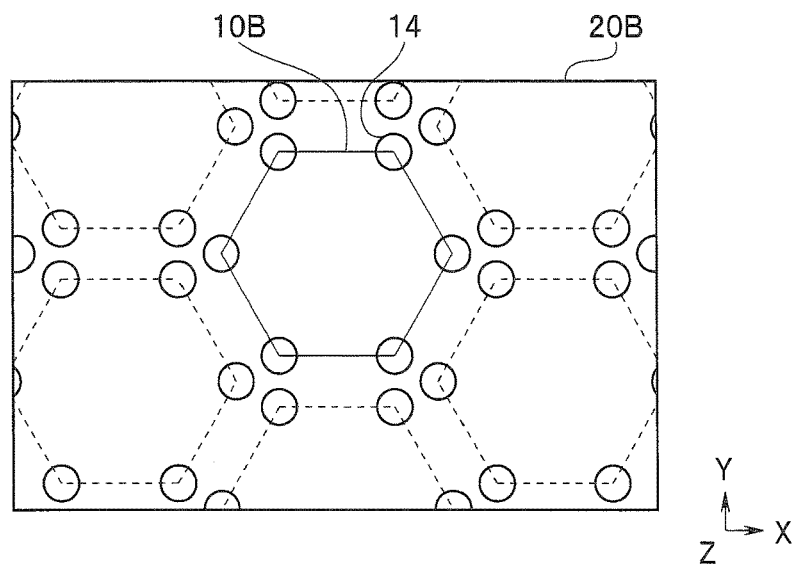
FIG. 10 is a schematic top view for illustrating an element of a third embodiment.

Since an element 20B of a third embodiment shown in FIG. 10 resembles the element 20 and the like, the same components are given the same reference numerals, and description thereof will be omitted.

In the element 20B, each cell 10B exclusively has six pillars 14. Therefore, useless areas which do not contribute to transmission/reception are formed among the cells 10B.

In the element 20 and the like in which adjoining cells 10 share a pillar 14, when one pillar is faulty, three cells 10 sharing the pillar become faulty. In comparison, in the element 20B, even if a pillar is in a bad condition, only one cell 10B becomes faulty. Therefore, a probability that the element 20B can be used as a product is high. That is, in the element 20B, there are a lot of cases where all the cells 10B are not necessarily required to be good items.

The element 20B has the effects of the element 20 and the like. Further, manufacturing yield of the element 20B is higher than that of the element 20 and the like.

Note that it is preferable that the aperture ratio be 90% or above in the element 20B also. Especially preferably, the element 20B may be designed so that the aperture ratio becomes 95%. Further, a part of the pillars may be shared by adjoining cells, with remaining pillars being exclusively possessed.

Fourth Embodiment

Figure 11:
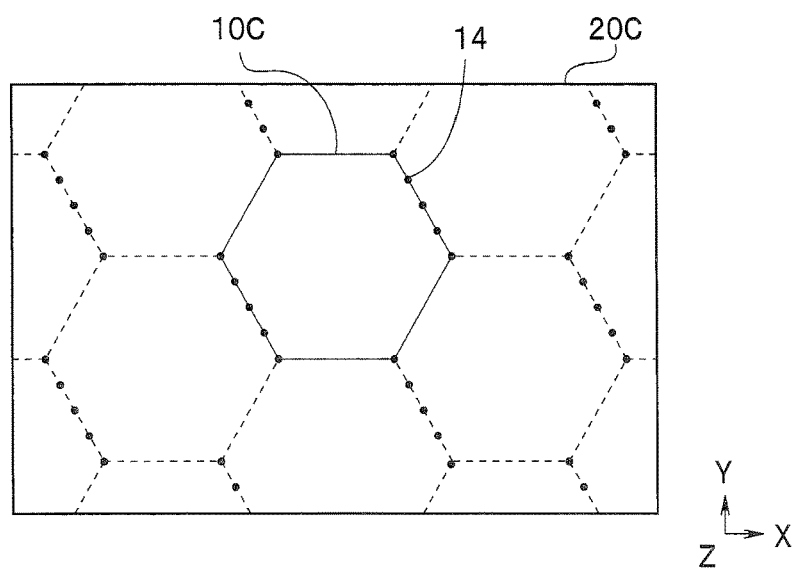
FIG. 11 is a schematic top view for illustrating an element of a fourth embodiment.

Since an element 20C of a fourth embodiment shown in FIG. 11 resembles the element 20 and the like, the same components are given the same reference numerals, and description thereof will be omitted. Note that, in the figure below, the pillars 14 are indicated by black circles indicating centers of the pillars 14.

In the element 20C, pillars 14 are arranged not only at six apexes of each regularly hexagonal cell 10C. Three pillars 14 are also arranged on each of two sides, which are borderlines with adjoining cells. That is, the membrane of the cell 10C is supported by twelve pillars 14.

Displacement of the membrane of the cell 10C is not in a six-fold symmetry relative to a center of the cell but in a two-fold symmetry, and the membrane is displaced in a complicated shape. Therefore, in the cell 10C, a width of a resonance frequency is wide.

The element 20C has the effects of the element 20. Further, an ultrasound generated by the membranes 18 is a wide-band ultrasound, and, similarly, transmission/reception of a wide-band ultrasound is possible.

Fifth Embodiment

Figure 12:
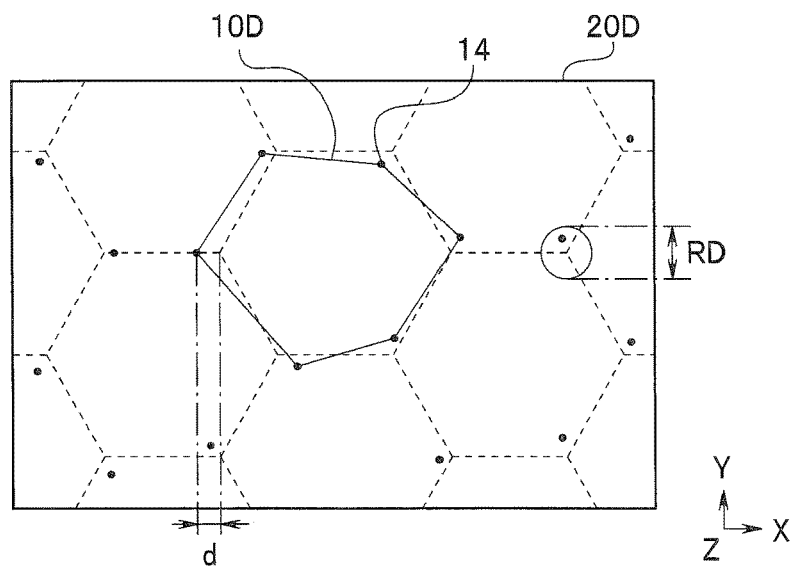
FIG. 12 is a schematic top view for illustrating an element of a fifth embodiment.

Since an element 20D of a fifth embodiment shown in FIG. 12 resembles the element 20 and the like, the same components are given the same reference numerals, and description thereof will be omitted.

In the element 20D, the pillars 14 are arranged not at apexes of regularly hexagonal cells 10D but at positions slightly deviated from the apexes. Though an amount of deviation d is set at random, the pillars 14 are set inside a circle with a diameter RD. It is preferable that the diameter RD be between 1/100 and 1/10 of the distance D, inclusive. Effects are remarkable within the above range. The amount of deviation d is set, for example, on the basis of a random number.

In a cell 10 in which the distances D among pillars 14 are the same, there is a possibility that unnecessary resonance occurs, or an unnecessary transverse wave occurs. In comparison, in the element 20D, since pillars 14 of each cell 10D are arranged at random with a slight planar displacement from apexes of a regular hexagon, the possibility that unnecessary resonance occurs does not exist.

That is, the element 20D has the effects of the element 20. Further, the possibility that unnecessary resonance occurs does not exist.

Sixth and Seventh Embodiments

Since an element 20E of a sixth embodiment and an element 20F of a seventh embodiment resemble the element 20 and the like, the same components are given the same reference numerals, and description thereof will be omitted.

Figure 13:
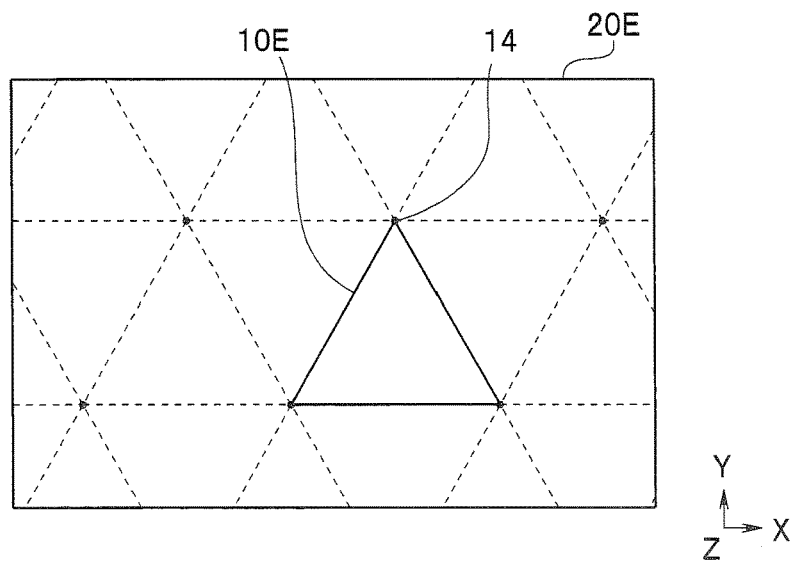
FIG. 13 is a schematic top view for illustrating an element of a sixth embodiment.
Figure 14:
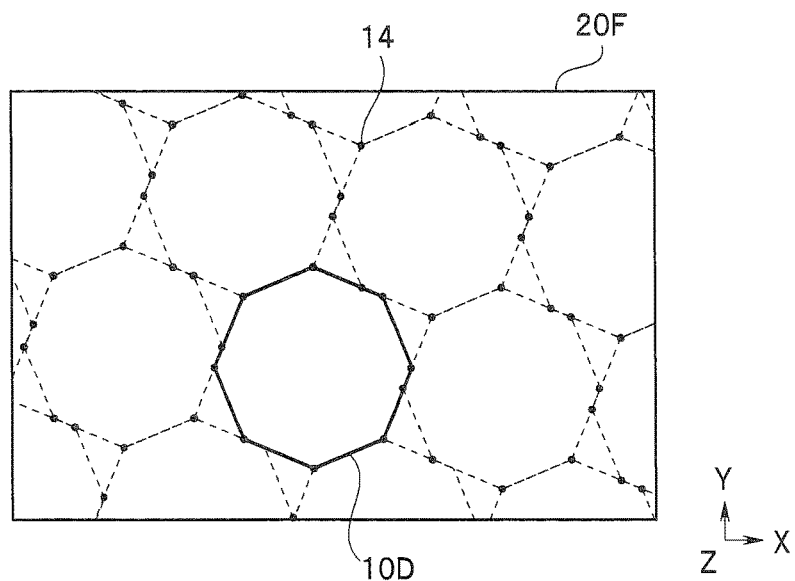
FIG. 14 is a schematic top view for illustrating an element of a seventh embodiment.

As shown in FIG. 13, regularly triangular cells 10E are closely arranged in the element 20E. That is, the membrane 18 of each cell 10E is supported by three common pillars 14. Further, as shown in FIG. 14, each cell 10F is regularly octagonal in the element 20F. The membrane 18 of each cell

10F is supported by twelve pillars 14, and eight among the twelve pillars are arranged at apexes of the regularly octagonal cell 10F.

The element 20E and the element 2OF have the same effects as the element 20. That is, if such transducer cells are provided that the cavities 14H are formed by the pillars 14 supporting the membranes 18, a number of the pillars supporting each transducer cell is not limited to six as long as it is three or larger. Note that it is preferable that the number of the pillars supporting each transducer cell be sixteen or fewer, and it is easy to increase the aperture ratio if the number is within the range or fewer.

A plane view shape of the membrane (cell) is not limited to a particular shape. For example, the plane view shape may be a parallelogram, a rectangle, a diamond shape or a trapezoid. Especially, a shape which enables a plurality of cells to be planarly filled, that is, which enables a plurality of cells to be closely arranged is favorable because it is easy to increase the aperture ratio.

Eighth to Eleventh Embodiments

Since an element 20G of an eighth embodiment to an element 20J of an eleventh embodiment resemble the element 20 and the like, the same components are given the same reference numerals, and description thereof will be omitted.

Figure 15:
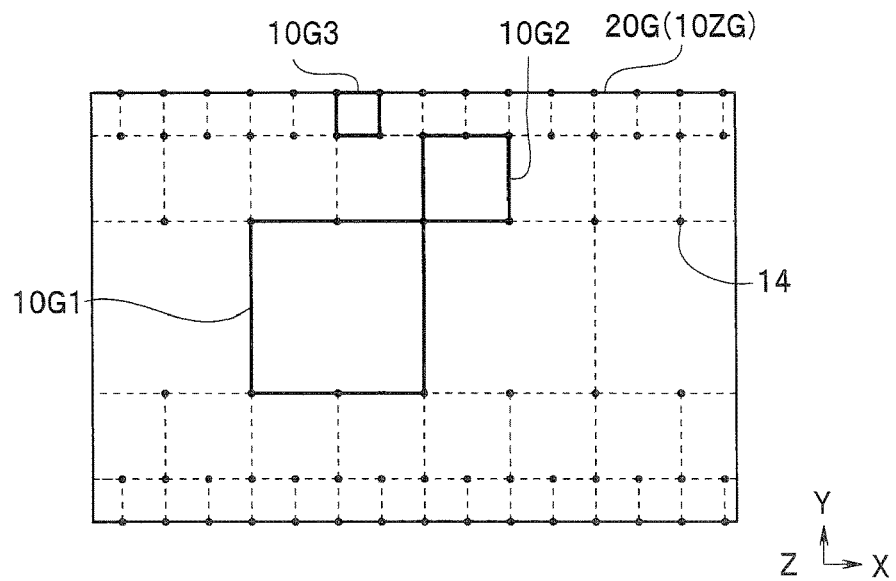
FIG. 15 is a schematic top view for illustrating an element of an eighth embodiment.

As shown in FIG. 15, a cell group 10ZG of the element 20G of the eighth embodiment is provided with three kinds of cells 10G1 to 10G3 having cavities in the same regularly square shape but having different sizes (plane view dimensions of the cells 10G).

Figure 16:
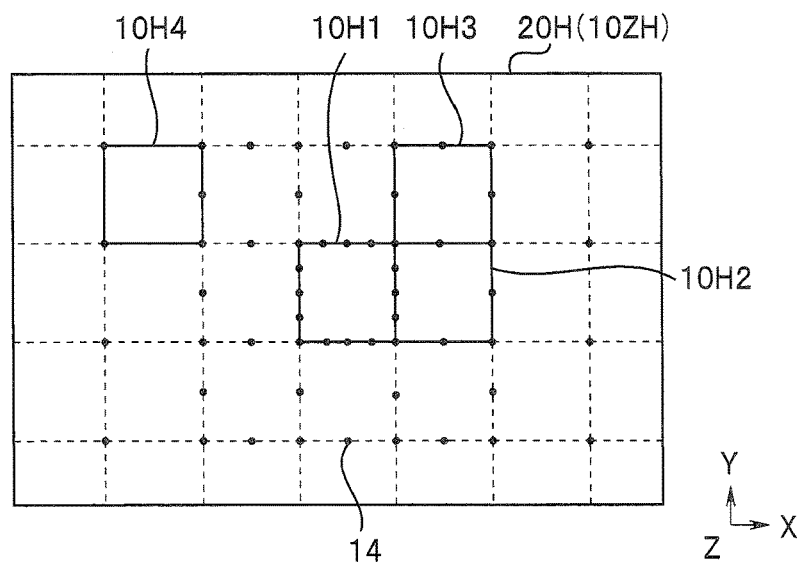
FIG. 16 is a schematic top view for illustrating an element of a ninth embodiment.

As shown in FIG. 16, a cell group 10ZH of the element 20H of the ninth embodiment is provided with four kinds of cells 10H1 to 10H4 having cavities in the same shape and with the same size but being different in a number of pillars 14 supporting each cavity.

Figure 17:
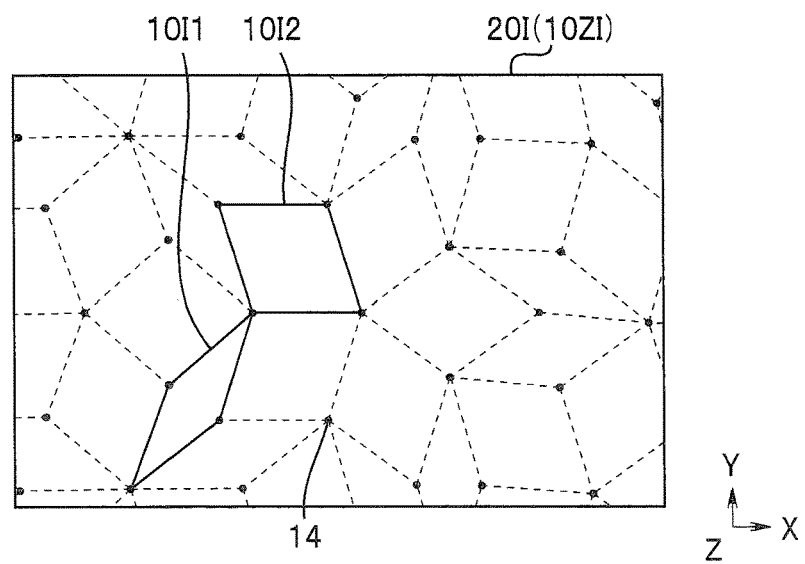
FIG. 17 is a schematic top view for illustrating an element of a tenth embodiment.

As shown in FIG. 17, a cell group 10ZI of the element 20I of the tenth embodiment is provided with two kinds of cells 10I1 and 10I2 which are different in the shape of the cavities (cells).

Figure 18:
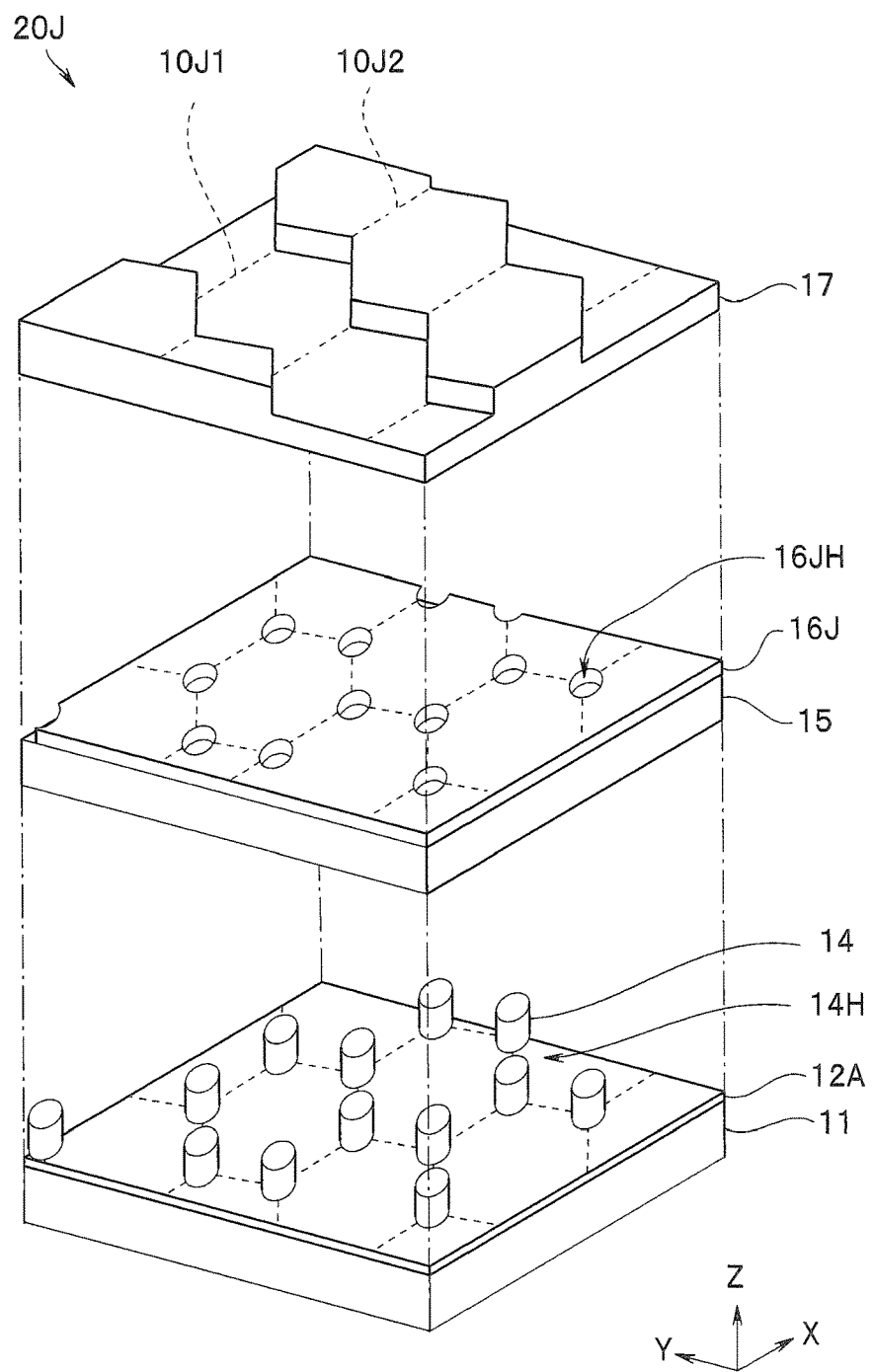
FIG. 18 is an exploded view of an element of an eleventh embodiment.

As shown in FIG. 18, a cell group 10ZJ of the element 20J of the eleventh embodiment is provided with two kinds of cells 10J1 and 10J2 having the same cavity shape and the like but being different in thickness of the membranes 18.

In a cell group, a plurality of kinds of cells that are different in at least any that is selected from among the plane view shape of the cavities, the size of the cavities (plane view dimension), the number of pillars, and the thickness of the membranes are different in the resonance frequency.

Therefore, a frequency band of an ultrasound which can be transmitted or received by the elements 20G to 20J is wide. For example, in the element 20G shown in FIG. 15, the largest cell 10G1 is arranged in a central part of the element 20G, and the smallest cell 10G3 is arranged on an outermost periphery. Since the frequency of an ultrasound generated by the large cell 10G1 is low, a beam easily spreads. Since the frequency of an ultrasound generated by the small cell 10G3 is high, a beam does not easily spread. In the element 20G, since the low-frequency cells are arranged in the central part, convergence of an ultrasound beam in the whole element is good.

On the other hand, in the element 20H shown in FIG. 16, since the membrane 18 of the cell 10H1 arranged in a central part is supported by sixteen pillars 14, a resonance frequency is high. In comparison, since the membrane 18 of the cell 10H4 arranged in a surrounding area is supported by five pillars 14, a resonance frequency is low. The membrane 18 of the cell 10H2 arranged between the cell 10H1 and the cell 10H3 is supported by ten pillars 14, and the membrane 18 of the cell 10H3 is supported by eight pillars 14. Therefore, resonance frequencies of the cell 10H2 and the cell 10H3 are between the resonance frequency of the cell 10H1 and the resonance frequency of the cell 10H4.

In the element 20H, observation with high resolution is possible on a near-point side of an observation target. That is, high resolution is possible on the near-point side because an image is formed by a high-frequency signal there.

Shapes of the two kinds of cells 10I1 and 10I2 of the element 20I shown in FIG. 17 are two kinds of diamond shapes constituting a Penrose tile pattern, and pillars are arranged at apexes of the two kinds of diamond shapes. In a Penrose tile pattern, two kinds of diamond shapes (a diamond shape with an acute angle of 72 degrees and an obtuse angle of 108 degrees, and a diamond shape with an acute angle of 36 degrees and an obtuse angle of 144 degrees) are planarly filled. In a case of filling using regular polygons, a periodic pattern appears. In the Penrose pattern, however, a periodic pattern does not appear unlike other plane filling.

Since the Penrose tile pattern has a specific symmetry of a five-fold symmetry, it does not have a translational symmetry when seen planarly. Therefore, unnecessary resonance seldom occurs in the element 20I, and the element 20I can be especially preferably used.

Note that, since a diamond-shaped cell shows a resonance frequency equal to that of a cell having an elliptical cavity of an almost same size, the element 20I has two kinds of resonance frequencies. Furthermore, an element having a plurality of cells obtained by reducing or expanding a Penrose tile pattern in one direction is a wide-band element which theoretically has ten kinds of resonance frequencies.

In the element 20J shown in FIG. 18, a resonance frequency of the cell 10J2 the membrane 18 of which has a larger thickness is higher than a resonance frequency of the cell 10J1 the membrane 18 of which has a smaller thickness. That is, a resonance frequency is in proportion to thickness of a membrane.

Note that arrangement of cells in an element having a plurality of kinds of cells which are different in the resonance frequency can be changed according to purposes. Further, a number of the kinds of cells may be two or more.

All of the elements 20G to 20J have the effects of the element 20 and the like and, further, have a wider-band characteristics. Therefore, the elements 20G to 20J can be applied to ultrasound Doppler measurement and the like. Further, arrangement of cells in consideration of directivity of a sound wave in an element, arrangement of cells having a high resolution and being excellent in convergence in an ultrasound beam, and the like are also possible according to purposes.

Further, by changing two or more factors selected from among a plane view shape of the cavities, the size of the cavities (plane view dimension), the number of pillars and the thickness of the membranes, a wide-band element having more resonance frequencies is obtained. Especially, by successively and gradually changing resonance frequencies of cells to be arranged, a very wide band element is obtained.

Note that, in the element 20J shown in FIG. 18, the lower electrodes 12A are formed on the whole surface of the area where the cell group is formed. On the other hand, though the upper electrodes 16J are also formed substantially on the whole surface of the area where the cell group is formed, holes 16JH are formed in areas facing the pillars 14. Areas of the membrane immediately above the pillars 14 are non-sensitive areas. However, since the upper electrode 16 does not exist in the non-sensitive areas in the element 20J, the reception sensitivity is higher.

Figure 19:
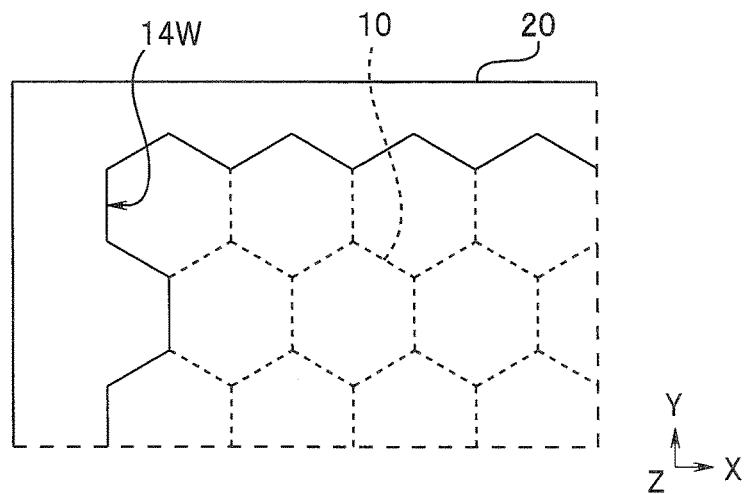
FIG. 19 is a top view of a sealing wall of the element of the embodiments.

Here, FIG. 19 shows an example of an end portion of the cell group 10Z of the element 20 described in the above embodiment. As already described, the plurality of cavities 14H of the cells 10 constituting the cell group 10Z communicate with one another. However, it is preferable that an outer peripheral side of cavities 14H in an outermost peripheral area of the cell group 10Z be surrounded by a sealing wall constituted by envelope surfaces, and the plurality of cavities 14H of the cell group 10Z form a sealed space which does not communicate with an outside. Note that, in the elements 20A to 20J also, it is preferable that the plurality of cavities 14H be sealed spaces which do not communicate with an outside.

In the element in which the plurality of cavities 14H of the cell group 10Z are sealed spaces which do not communicate with the outside, an inner pressure in the cavities 14H do not change even if a surrounding environment changes. Therefore, there is not a possibility that the transmission/reception sensitivity changes.

Twelfth Embodiment

The elements 20 to 20J described above can be preferably used for an ultrasound endoscope (hereinafter referred to as an "endoscope") 2.

Figure 20:
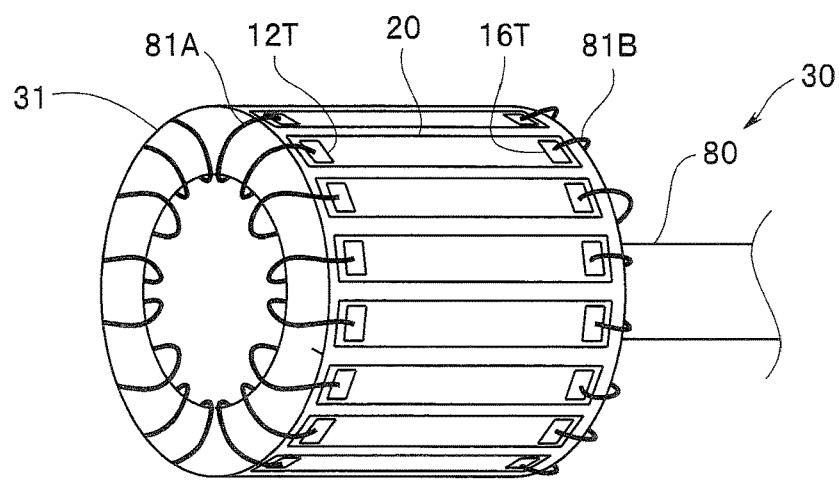
FIG. 20 is a perspective view of an array-type ultrasound transducer of an ultrasound endoscope of a twelfth embodiment.

As shown in FIG. 20, a radial-type and array-type ultrasound transducer 30 has a plurality of elements 20, a cylindrical holding member 31 with the elements 20 arranged on an outer surface thereof, and a cable 80. The lower electrode terminals 12T and the upper electrode terminals 16T of the elements 20 are connected to conductor wires 81A and 81B of the cable 80, respectively. Note that the ultrasound array may be of a convex type, a linear type or the like.

Figure 21:
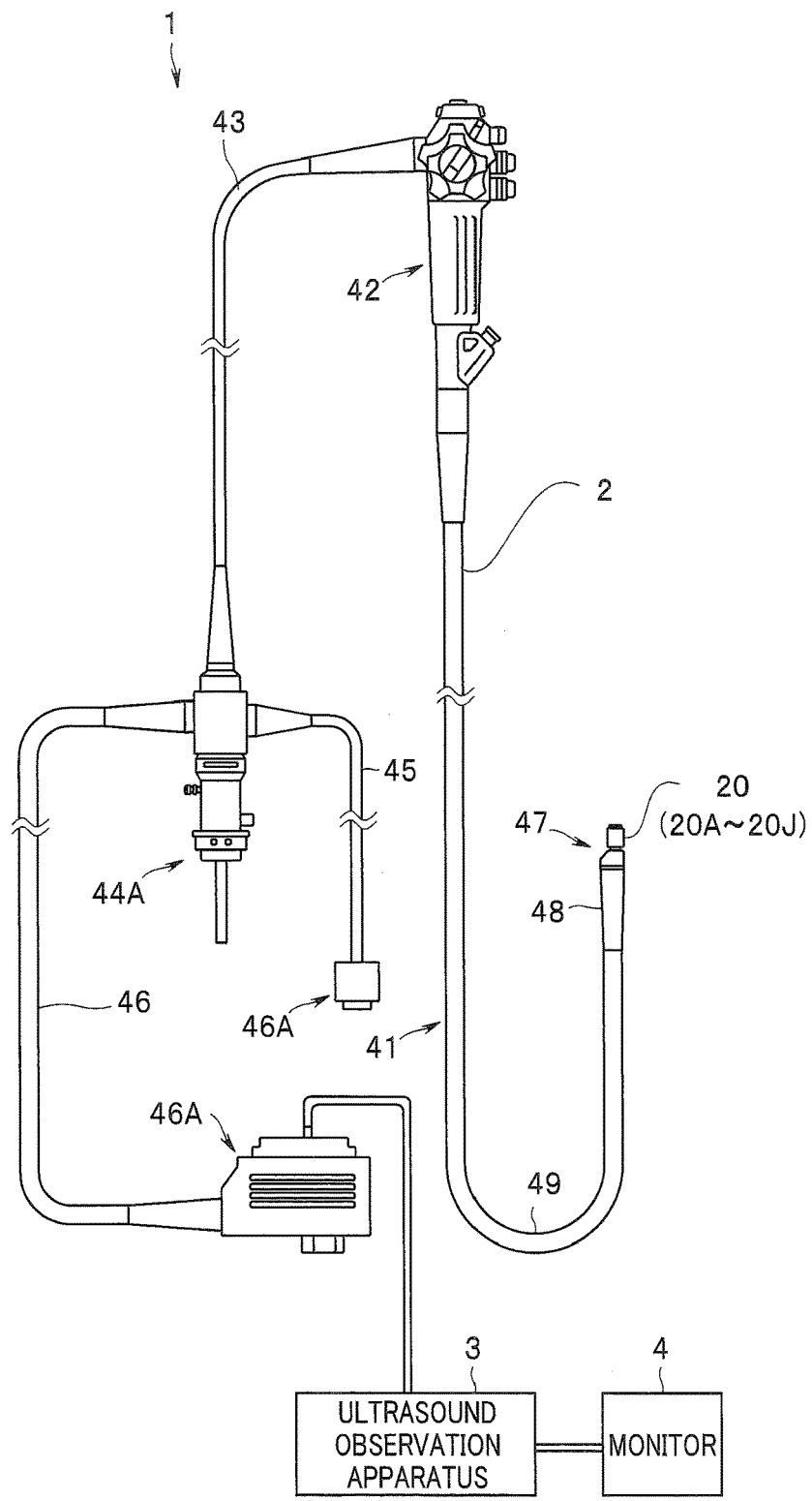
FIG. 21 is an external view of the ultrasound endoscope of the twelfth embodiment.

FIG. 21 shows an ultrasound endoscope system 1 having the ultrasound endoscope 2 of the twelfth embodiment with the array-type ultrasound transducer 30 (elements 20) arranged at a distal end portion 47 thereof. The ultrasound endoscope 2 constitutes the ultrasound endoscope system 1 together with an ultrasound observation apparatus 3 and a monitor 4. The ultrasound endoscope 2 is provided with an elongated insertion portion 41 to be inserted into a body, an operation portion 42 arranged at a proximal end of the insertion portion 41, and a universal cord 43 extending from a side part of the operation portion 42.

A connector 44A connected to a light source apparatus (not shown) is arranged at a proximal end portion of the universal cord 43. A cable 45 to be detachably connected to a camera control unit (not shown) via a connector 45A and a cable 46 to be detachably connected to the ultrasound observation apparatus 3 via a connector 46A extend from the connector 44A. The monitor 4 is connected to the ultrasound observation apparatus 3.

The insertion portion 41 is configured by connecting the distal end portion 47, a bending portion 48 positioned at a rear end of the distal end portion 47, and a long flexible tube portion 49 having a short diameter and flexibility, which is positioned at a rear end of the bending portion 48 and extends to the operation portion 42, in that order from a distal end side. The array-type ultrasound transducer 30 is arranged on a distal end side of distal end portion 47. The endoscope 2 acquires an ultrasound image by the array-type ultrasound transducer 30 arranged at the distal end portion 47.

The endoscope 2 is provided with the ultrasound transducer elements with a high ultrasound transmission sensitivity and a high ultrasound reception sensitivity and, therefore, is able to acquire a high-resolution image.

Note that it goes without saying that the elements 20 to 20J can be arranged not only in the endoscope 2 shown in FIG. 21 but also in various small-sized ultrasound diagnostic apparatuses requiring diameter reduction, for example, an IVUS (intra vascular ultrasound) apparatus, an external ultrasound probe or a capsule-type ultrasound endoscope.

The present invention is not limited to the embodiments and the like described above. Various modifications and improvements, for example, a combination of components of the embodiments are possible within a range not departing from the spirit of the present invention.

What is claimed is:

1. An ultrasound transducer element comprising:
   a cell group comprising a plurality of ultrasound transducer cells, each of the plurality of ultrasound transducer cells comprising:
      a lower electrode arranged on a substrate,
      a membrane including an upper electrode arranged facing the lower electrode with a cavity portion positioned between the lower electrode and the upper electrode, and
      a plurality of pillars forming the cavity portion to support the membrane,
   wherein each cavity portion mutually communicates with other cavity portions;
   the plurality of pillars comprises groups of six pillars where each group supports a corresponding portion of the membrane;
   the plurality of pillars are cylindrical in cross-section and a diameter of the plurality of pillars is between $\frac{1}{20}$ and $\frac{1}{5}$ of a distance between adjacent pillars;
   the lower electrode comprises a plurality of lower electrode portions each corresponding to one of the groups of six pillars, the plurality of lower electrode portions being connected to each other by a lower electrode wiring; and
   the upper electrode comprises a plurality of upper electrode portions each corresponding to one of the groups of six pillars, the plurality of upper electrode portions being connected to each other by an upper electrode wiring.

2. The ultrasound transducer element according to claim 1, wherein each pillar supports membranes corresponding to a plurality of adjoining ultrasound transducer cells.

3. The ultrasound transducer element according to claim 2, wherein at least either the lower electrode or the upper electrode of the ultrasound transducer cell is an electrode common to the plurality of ultrasound transducer cells, the common electrode being arranged on a whole surface of a cell group forming area of the substrate.

4. The ultrasound transducer element according to claim 2, wherein the cell group comprises a plurality kinds of the ultrasound transducer cells that are different in at least any that is selected from among a shape of the cavity, a size of the cavity, the number of pillars and a thickness of the membrane.

5. The ultrasound transducer element according to claim 2, wherein
   shapes of the respective cavities include two kinds of diamond shapes constituting a Penrose tile pattern; and the pillars are arranged at apexes of the two kinds of diamond shapes.

6. The ultrasound transducer element according to claim 2, wherein an outer peripheral side of the cavity portions in an outermost peripheral area of the cell group is surrounded by a sealing wall comprising envelope surfaces, and the cavity portions of the cell group are sealed spaces that do not communicate with an outside.

7. An ultrasound endoscope comprising:
 an insertion portion comprising the ultrasound transducer element according to claim 1 arranged at a distal end portion of the insertion portion,
 an operation portion arranged on a proximal end side of the insertion portion, and
 a universal cord extending from the operation portion.

* * * * *